United States Patent [19]

Lorenz et al.

[11] 4,348,887
[45] Sep. 14, 1982

[54] APPARATUS FOR DETERMINING THE EFFECTS OF DILUTION AND/OR DIFFUSION ON THE GASEOUS COMPONENTS OF A GAS FLOW

[75] Inventors: Hans-Walther Lorenz, Hamburg; Gerd Schumacher, Pinneberg; Helmut Kirchner, Hamburg, all of Fed. Rep. of Germany

[73] Assignee: B.A.T. Cigaretten-Fabriken GmbH, Hamburg, Fed. Rep. of Germany

[21] Appl. No.: 174,573

[22] Filed: Aug. 4, 1980

[30] Foreign Application Priority Data

Aug. 3, 1979 [DE] Fed. Rep. of Germany ....... 2931647

[51] Int. Cl.$^3$ ............................................. G01N 31/08
[52] U.S. Cl. ............................................ 73/23; 73/38
[58] Field of Search ............................ 73/38, 23, 1 G

[56] References Cited

U.S. PATENT DOCUMENTS 3,115,767 12/1963 Tyrrell et al. ............................ 73/38
3,460,374  8/1969 Parks ....................................... 73/23
4,171,635 10/1979 Calleson et al. ........................ 73/38

OTHER PUBLICATIONS

Muramatsu, M., et al., *A Model Study on the Diffusion and Dilution of Low Molecular Weight Gaseous Compounds Through Cigarette Paper During Smoking*, In Beitrage zur Tabakforschung, Band 9, Heft 3, pp. 141-146, Oct. 1977.

*Primary Examiner*—Kyle L. Howell
*Assistant Examiner*—Joseph W. Roskos
*Attorney, Agent, or Firm*—Armstrong, Nikaido, Marmelstein & Kubovcik

[57] ABSTRACT

An apparatus for determining the effect of dilution and/or diffusion of the gaseous components of a gas flow passing through a gas permeable test object is claimed. The apparatus comprises a source of calibrating gas, a laminar resistance coupled to the source of calibrating gas with the gas flowing through the laminar resistance, and a volumeter is coupled to the laminar resistance for measuring the volume of gas flowing therethrough. The gas from the laminar resistance flows through the test object to a gas concentration measuring device for receiving and for measuring the concentration thereof. A bypass device is provided for bypassing the flow of gas around the test object, and a suction device draws gas from the source to the measuring device.

9 Claims, 2 Drawing Figures

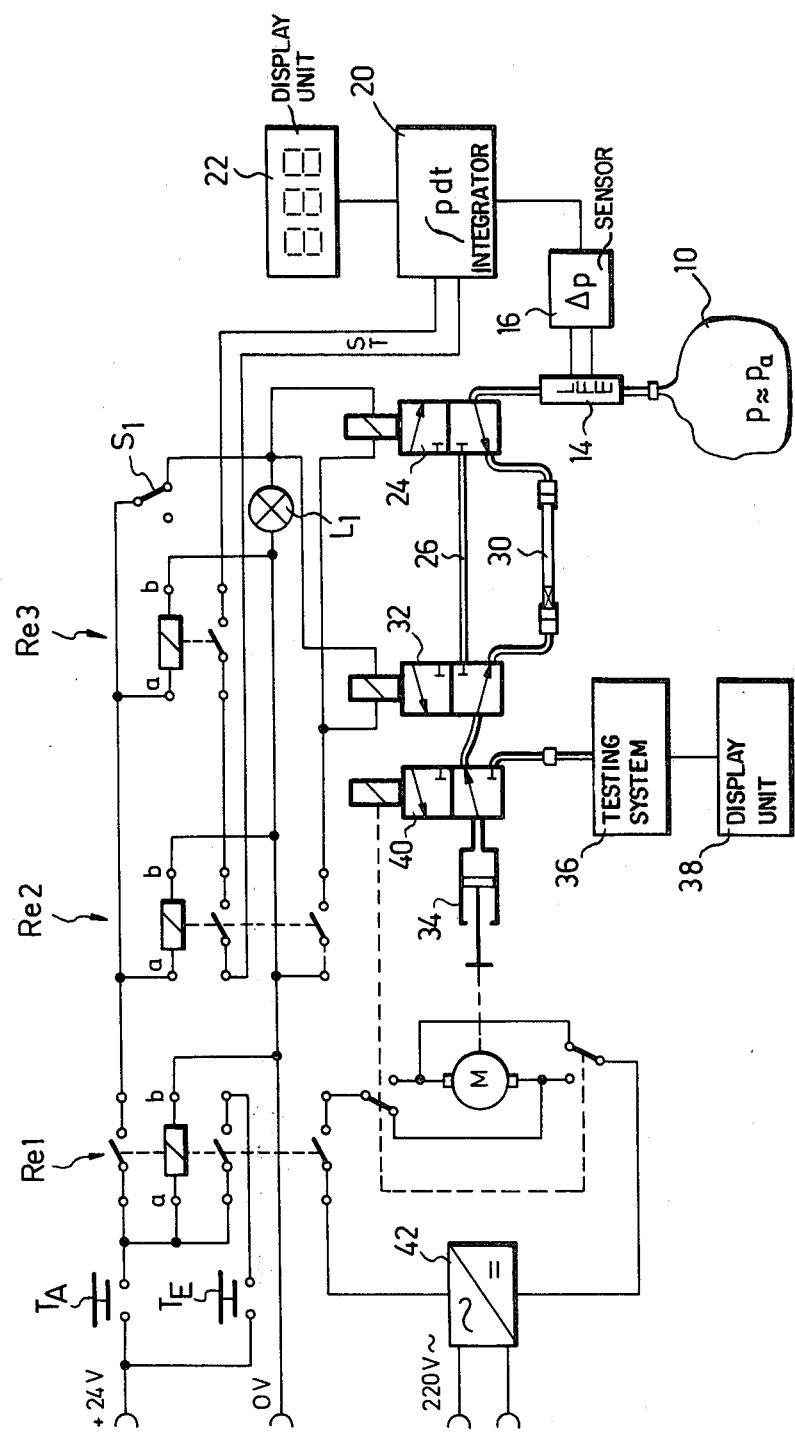

APPARATUS FOR DETERMINING THE EFFECTS OF DILUTION AND/OR DIFFUSION ON THE GASEOUS COMPONENTS OF A GAS FLOW

BACKGROUND OF THE INVENTION

1. Field of the Invention

The invention concerns apparatus for determining the effects of dilution and/or diffusion on the gaseous components of a gas flow passing through a gas-permeable test-object, with a suction source drawing a calibrating gas at least through part of the test-object, a volumeter for the calibrating gas flowing into the test-object and a concentration testing means for the gas issuing from the test-object. Such apparatus is suited for testing arbitrary gas-permeable test-objects, for instance filter plugs, filter rods, cigars and cigarettes.

2. Description of the Prior Art

While many publications have examined the changes in concentration of the mainstream smoke of cigarettes during combustion, the effects of dilution and diffusion on the concentration of gaseous components on account of the experimental difficulties involved have been researched only recently. This is because the effects of diffusion and dilution could not be empirically distinguished from the combustion-induced generation of gases.

However, as the gaseous components of the smoke, in particular the so-called low-molecular weight gases such as nitrogen, hydrogen, methane, carbon monoxide, carbon dioxide and nitric oxides have become significant, apparatus was developed to determine the effects of dilution and diffusion on the gaseous components of the cited species in the flow of smoke (BEITRAEGE ZUR TABAKFORSCHUNG, vol. 9, issue 3, October 1977, pp 141).

In that procedure, a calibrating gas is drawn out of a gas pouch and through a cigarette by a smoking machine and then is analyzed quantitatively, that is, the concentration of the gas in the flow issuing from the cigarette is determined. Prior to each test series, the calibrating gas is made to pass through a soap-bubble buret to determine the volume of the calibrating gas flowing into the cigarette. Given the constant stroke of the smoking machine and hence the constant volume aspirated by the smoking machine, the volume of the calibrating gas flowing into the cigarette and the measured concentration of the issuing gas, the change in concentration of the calibrating gas can be ascertained, which is due to the diffusion of the calibrating gas through the cigarette paper outward and also to the ambient gas rarefying the calibrating gas which is aspirated through the cigarette paper into the cigarette. The calibrating gas is made to pass from a compressed gas contained into the gas pouch because the calibrating gas' pressure may not exceed that of the atmosphere around the cigarette.

In practice, especially in routine monitoring tests on cigarettes, there were several drawbacks in this prior art apparatus. First, operating a soap-bubble buret is extremely complex, time-consuming and susceptible to errors. Second, the concentration of a calibrating gas passed from the gas bottle into the gas pouch and the gas pouch on account of inadequate seals, had an influx of foreign gas during handling, and residual gases due to incomplete evacuation of the gas pouch. The system was thus susceptible to variations which could not be checked unless there was access into the otherwise closed measuring system.

Lastly, the flow rate of the gas entering the cigarette can not be measured during the testing properly because the calibrating gas passed through the soap-bubble buret can't be used for measuring the dilution and diffusion in view of the water vapor that was absorbed.

SUMMARY OF THE INVENTION

It is therefore the object of the invention to create apparatus for determining the effects of dilution and diffusion on the gaseous components of a gas flow in which the above cited drawbacks are eliminated.

We propose in particular an apparatus which in spite of simple handling permits the precise monitoring and calibration of the various parameters affecting the measurements.

The advantages obtained by the invention in particular rest on the volumeter being constantly inserted between the gas source and a cigarette, for example that is, that the volume of the calibrating gas flowing into the cigarette is simultaneously ascertained with each stroke of a smoking machine, without thereby degrading the measurement properly. This volume therefore is known for each measurement, whereby any fluctuations in the volume of the calibrating gas used can be accounted for in the analysis.

By hooking the bypass into the flow path, the calibrating gas passes from the gas source over the laminar resistance used for volumetry and past the cigarette to the testing means for the calibrating gas concentration. Using this procedure, the calibration of the volumeter can easily be monitored.

The volume aspirated by the smoking machine remains precisely constant even over prolonged periods of time, whereby this known volume can be correlated with the display of the volumeter when flow takes place through the bypass, and hence the volumeter can be calibrated.

Furthermore, this procedure permits single and rapid checking of the concentration of the calibrating gas flowing into the cigarette without penetrating the closed measuring system. Therefore, changes in the calibrating gas concentration also can be rapidly detected in this manner and be taken into account in later analysis.

BRIEF DESCRIPTION OF THE DRAWINGS

The invention is explained below in further detail in relation to illustrative embodiments and the attached, schematic drawings.

FIG. 2 is a detailed switching circuit for the apparatus of the present invention.

DETAILED DESCRIPTION OF THE PREFERRED EMBODIMENT

Figure 1:
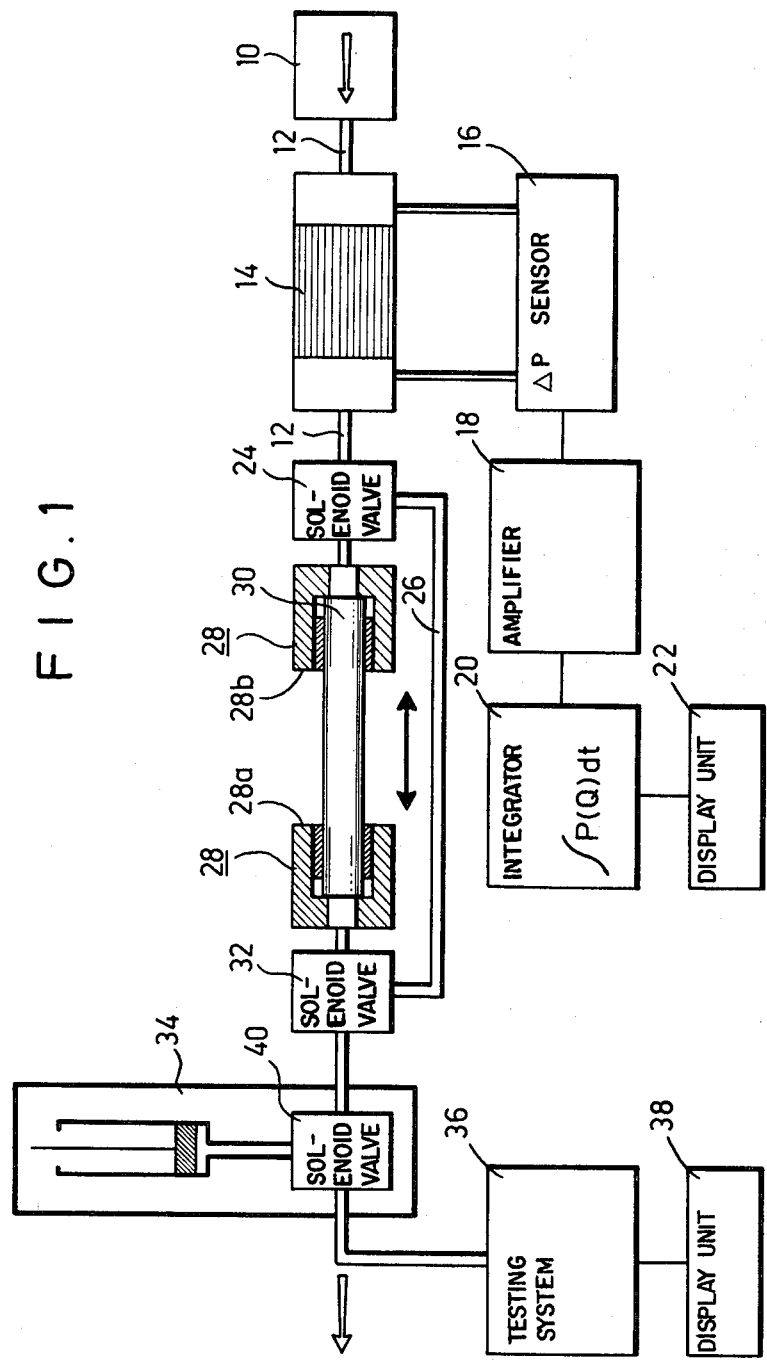
FIG. 1 is a block circuit diagram of the present invention.

As shown in FIG. 1, the apparatus of the invention comprises a source 10 for a calibrating gas, for instance a gas pouch, into which the calibrating gas is fed from a bottle (not shown). This gas source 10 is connected to a flow conduit 12. A laminar resistance 14 is connected together with the gas source 10 to the flow conduit 12; a pressure drop of the calibrated gas aspirated by the piston smoking machine 34 takes place in the resistance 14. The pressure difference created at the laminar resistance 14 is detected by pressure-difference pick-up 16 and fed to an amplifier 18. The amplified pressure difference signal is applied to an integrator 20 which integrates the pressure difference over the time of flow. The output signal from the integrator 20 is a direct measure of the volume of calibrating gas withdrawn in one stroke from the gas source 10 and is shown in a display unit 22.

After flowing through the laminar resistance 14, the calibrating gas arrives at a first solenoid valve 24. Depending on the position of this solenoid valve 24, the calibrating gas either flows through a bypass 26 or through a test-object, held in a fastener 28, in this case a cigarette. The two heads 28a and 28b of the fastener may be displaced relative to each other, as indicated by arrow A in FIG. 1. The ends of the cigarette 30 are hermetically received in the heads 28a and 28b, so that only the surface of cigarette 30 between the heads 28a and 28b is in contact with the ambient atmosphere. Thus a gas exchange if any can take place only through this precisely defined region through the cigarette paper between the inside of the cigarette and the ambient atmosphere. This region of the surface can be varied by displacing the heads 28a and 28b as needed.

The feedback of the gas flowing through the bypass 26 into the main flow path, i.e. the path of flow through the cigarette 30 takes place through a second solenoid valve 32. The output of the second solenoid valve 32 is connected to a third solenoid valve 40 which is connected to the piston smoking machine and a testing system 36, shown only schematically, for the concentration of the calibrating gas present in the volume of gas. The type of measuring system 36 depends on the kind of the gas being examined. When several gases are tested simultaneously, a gas chromatograph is used for instance. When only a specific gas is being examined, for instance CO, an infra-red instrument for continuous measurement at each stroke is appropriate. The test result is shown in a display unit 38. A piston smoking machine 34 at each piston stroke aspirates a constant volume of gas and expels same on the piston return stroke.

The operation of this apparatus is explained hereunder in closer detail in relation to FIG. 2, which shows a switching circuit of the apparatus, including the already cited components and keys $T_A$ and $T_E$ for switching on the various components, relays Re1, Re2 and Re3 for controlling the various components, a motor M for the smoking machine 34, a switch $S_1$ for the first solenoid valve 24 and a display lamp $L_1$.

A conventional supply voltage of 24 v is applied to the keys and relays, and the motor M is driven by a 220 v source. As a DC motor is appropriately used, this line voltage must also be rectified in a rectifier 42.

The key $T_A$ is actuated manually, whereby the relay Re1 is energized and becomes self-latching. Thereby the relay Re1 switches on the motor M of the piston smoking machine 34 which then begins a stroke. Simultaneously, the relay Re1 applies the supply voltage to the relays Re2 and Re3. The relay Re2 actuates the two solenoid valves 32 and 24, which can be interrupted by a switch $S_1$. The position of the two solenoid valves is indicated by lamp $L_1$. After a time delay of 0.5 seconds, relay Re3 energized, thereby interrupting the start line to integrator 20.

The smoking machine 34 thus draws in a precisely defined volume of gas in one stroke, aspirating a definite amount of gas from the gas pouch 10. This amount flows through the laminar resistance 14 where the differential volume of flow is measured over the entire aspiration time in the manner explained above, the integration being carried out over the time of flow and being represented in the display unit 22. Therefore, the integration of the pressure difference and hence the measurement of volume begins at a precisely defined time determined by relay Re3.

The calibrating gas flows from the laminar resistance 14 to the solenoid valve 24, the position of which is determined by the switch $S_1$. Depending on that position, the calibrating gas flows either through the bypass 26 or through the cigarette 30. Thereupon the gas flows through the second, correspondingly set solenoid valve 32 and the third solenoid valve 40 into the smoking machine 34. When the piston of the smoking machine 34 reaches its end position, the end position key $T_E$ is actuated, thereby cancelling the self-latching of the relay Re1. This reverses the direction of rotation of the motor M, whereby the piston of the smoking machine 34 is moved back into its initial position and hence the gas volume is expelled from the smoking machine 34. The third solenoid valve 40 is switched over synchronously with the reversal of the direction of rotation of the motor M, whereby the volume of gas expelled from the smoking machine 34 flows into the measuring unit 36 which feeds the ascertained value into the display unit 38.

To calibrate the apparatus, in particular to monitor the calibration gas concentration and the volume of flow entering the cigarette, the first and second concentration valves 24, 32 are so set that the calibrating gas passes through the bypass 26, whereas in the actual measurement, the solenoid valves 24, 32 are switched and the calibrating gas will flow through the cigarette 30. From the constant volume aspirated by the smoking machine 34, the concentration of the calibrating gas flowing into the cigarette 30 and the measured concentration of the gas issuing from cigarette 30, it is then possible to compute the intensity of dilution of the gas on account of the ambient gases that flowed into the cigarette (for instance air) and on account of any diffusion of the calibrating gas out of the cigarette.

The present invention may be embodied in other specific forms without departing from the spirit or essential characteristics thereof. The presently disclosed embodiments are, therefore, to be considered in all respects as illustrative and not restrictive, the scope of the invention being indicated by the appended claims, rather than the foregoing description, and all changes which come within the meaning and range of equivalency of the claims are, therefore, to be embraced therein.

What is claimed is:

1. An apparatus for determining the effect of dilution and/or diffusion of the gaseous components of a gas flow passing through a gas permeable test object said apparatus comprising:
  (a) a source of calibrating gas;
  (b) laminar resistance means coupled to said source of calibrating gas, said gas flowing through said laminar resistance means;
  (c) volumeter means coupled to said laminar resistance means for measuring the volume of gas flowing therethrough;
  (d) a test object, wherein said gas from said laminar resistance means flow through said test object;

(e) gas concentration measuring means for receiving gas from said test object and for measuring the concentration thereof;
(f) bypass means for bypassing the flow of gas around said test object; and
(g) suction means for drawing air from said source to said measuring means.

2. An apparatus as set forth in claim 1, wherein said volumeter means comprises:
(a) pressure differential means for measuring the pressure differential across said laminar resistance means;
(b) integrator means for integrating the pressure differential and producing an output indicating the volume of gas flow through said laminar resistance means; and
(c) display means for displaying the volume of gas flow.

3. An apparatus as set forth in any of claims 1 or 2, including first solenoid valve means having a first port connected to said laminar resistance means and second and third ports connected to said test body and said bypass means, wherein said first solenoid valve directs flow from said laminar resistance means to either said test body or said bypass means.

4. An apparatus as set forth in claim 3, including a second solenoid valve means having one port connected to said test object, a second port connected to said bypass means and a third port connected to said suction means.

5. An apparatus as set forth in claim 4, including a third solenoid valve means having a first port coupled to said second solenoid valve means, a second port connected to said suction means and a third port connected to said measuring means.

6. An apparatus as set forth in claim 5, wherein said suction means comprises a smoking machine having an adjustable draw volume and including a piston and means for automatically returning said piston to an initial position when it reaches an end position and for switching said third solenoid valve means to connect said suction means to said measuring means.

7. An apparatus as set forth in any of claims 1 or 2, wherein said suction means comprises a smoking machine having an adjustable draw volume.

8. An apparatus as set forth in claim 7, wherein said smoking machine includes a piston and means for automatically returning said piston to an initial position when it reaches an end position thereby expelling the aspirated volume of gas.

9. An apparatus as set forth in claim 7, wherein said means for automatically returning said piston includes motor means for driving said piston and switching means for controlling the operation of said motor means.

* * * * *